United States Patent
White et al.

(10) Patent No.: US 10,413,241 B2
(45) Date of Patent: Sep. 17, 2019

(54) APPARATUS, METHOD AND COMPUTER PROGRAM FOR DETECTING PHYSIOLOGICAL PARAMETERS

(71) Applicant: Nokia Technologies Oy, Espoo (FI)

(72) Inventors: Richard White, Cambridgeshire (GB); Stefano Borini, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 321 days.

(21) Appl. No.: 14/904,938

(22) PCT Filed: Jun. 25, 2014

(86) PCT No.: PCT/FI2014/050516
§ 371 (c)(1),
(2) Date: Jan. 13, 2016

(87) PCT Pub. No.: WO2015/007949
PCT Pub. Date: Jan. 22, 2015

(65) Prior Publication Data
US 2016/0143587 A1    May 26, 2016

(30) Foreign Application Priority Data

Jul. 16, 2013 (GB) .................................. 1312720.4

(51) Int. Cl.
*A61B 5/01* (2006.01)
*A61B 5/00* (2006.01)

(52) U.S. Cl.
CPC .............. *A61B 5/6844* (2013.01); *A61B 5/01* (2013.01); *A61B 5/4266* (2013.01); *A61B 5/681* (2013.01);
(Continued)

(58) Field of Classification Search
CPC ....... A61B 5/6844; A61B 5/01; A61B 5/4266; A61B 5/681; A61B 5/6824; A61B 2562/0257; A61B 2562/04; A61B 2562/06
(Continued)

(56) References Cited

U.S. PATENT DOCUMENTS 8,352,004 B2 *  1/2013  Mannheimer ...... A61B 5/14552
                                                      600/310
8,855,734 B2 * 10/2014  Mannheimer ...... A61B 5/14552
                                                      600/310
(Continued)

FOREIGN PATENT DOCUMENTS

EP       2567655       3/2013
JP     2001078966      3/2001
(Continued)

OTHER PUBLICATIONS

International Search Report and Written Opinion received for corresponding Patent Cooperation Treaty Application No. PCT/FI2014/050516, dated Oct. 28, 2014, 15 pages.
(Continued)

*Primary Examiner* — Navin Natnithithadha
(74) *Attorney, Agent, or Firm* — Harrington & Smith

(57) ABSTRACT

An apparatus, method and computer program where the apparatus comprises: a plurality of sensors (3, 5) configured to detect a physiological parameter: wherein at least one first (5) sensor is configured to have a first sensitivity to the physiological parameter and at least one second sensor (3) is configured to have a second sensitivity to the physiological parameter; such that a parameter profile, comprising a plurality of measurements of the physiological parameter at different is provided by the apparatus.

23 Claims, 5 Drawing Sheets

Figure 3:
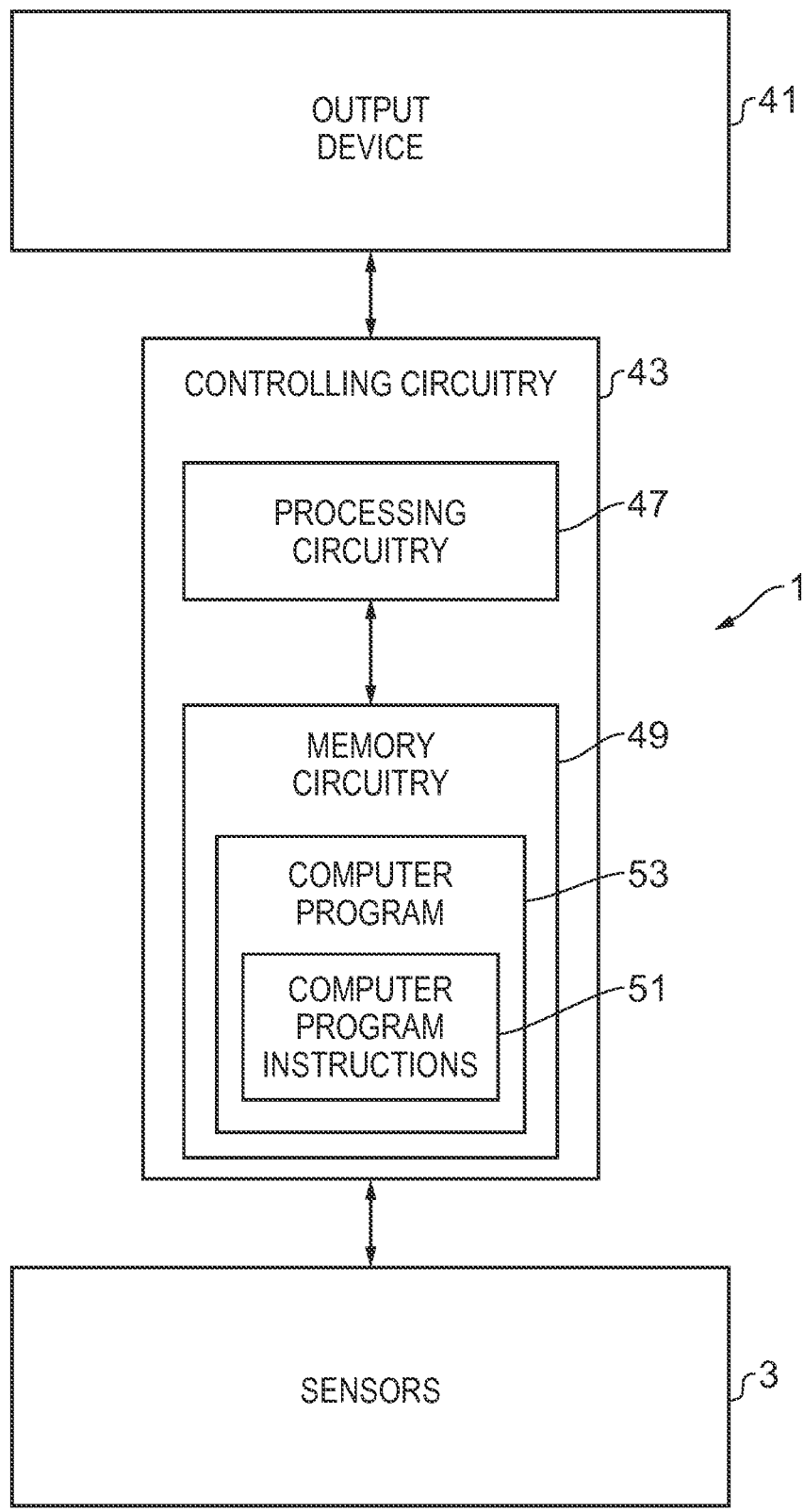

(52) U.S. Cl.
CPC ..... *A61B 5/6824* (2013.01); *A61B 2562/0257* (2013.01); *A61B 2562/04* (2013.01); *A61B 2562/06* (2013.01)

(58) Field of Classification Search
USPC .................................. 600/307, 309, 345–366
See application file for complete search history.

(56) References Cited

U.S. PATENT DOCUMENTS

| | | | |
|---|---|---|---|
| 9,380,949 B2* | 7/2016 | Schuessler | A61B 5/02055 |
| 9,592,007 B2* | 3/2017 | Nuovo | A61B 5/0022 |
| 9,603,560 B2* | 3/2017 | Monty | A61B 5/1477 |
| 2004/0260154 A1 | 12/2004 | Sidelnik et al. | |
| 2007/0191729 A1 | 8/2007 | Park et al. | |
| 2008/0306362 A1* | 12/2008 | Davis | A61B 5/14521 |
| | | | 600/307 |
| 2009/0182526 A1 | 7/2009 | Quinn et al. | |
| 2010/0179403 A1 | 7/2010 | Martinsen et al. | |
| 2011/0105910 A1* | 5/2011 | Lawson | G01J 5/0003 |
| | | | 600/474 |
| 2011/0257521 A1 | 10/2011 | Fraden | |
| 2012/0143022 A1 | 6/2012 | Lee et al. | |
| 2013/0079605 A1* | 3/2013 | Bandaru | A61B 5/6833 |
| | | | 600/310 |
| 2013/0197319 A1* | 8/2013 | Monty | A61B 5/1477 |
| | | | 600/301 |
| 2014/0316229 A1* | 10/2014 | Tognetti | A61B 5/0205 |
| | | | 600/383 |
| 2015/0157220 A1* | 6/2015 | Fish | A61B 5/0055 |
| | | | 600/301 |
| 2015/0160048 A1* | 6/2015 | Schuessler | A61B 5/02055 |
| | | | 73/866.5 |
| 2015/0335283 A1* | 11/2015 | Fish | A61B 5/02416 |
| | | | 600/324 |
| 2015/0335284 A1* | 11/2015 | Nuovo | A61B 5/0022 |
| | | | 600/301 |
| 2016/0022210 A1* | 1/2016 | Nuovo | A61B 5/681 |
| | | | 600/301 |

FOREIGN PATENT DOCUMENTS

| | | |
|---|---|---|
| WO | 03051191 | 6/2003 |
| WO | 2013080904 | 6/2013 |

OTHER PUBLICATIONS

Search Report received for corresponding GB Patent Application No. 1312720.4, dated Dec. 23, 2013, 3 pages.

* cited by examiner

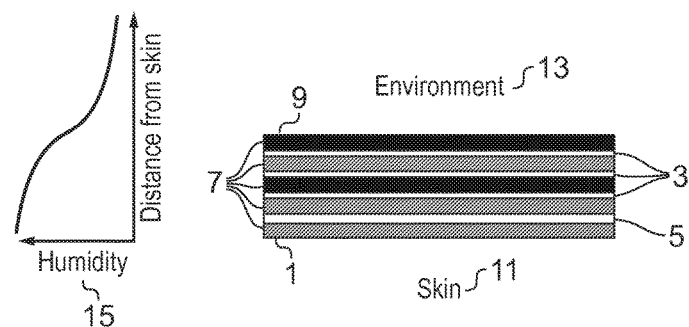
FIG. 1
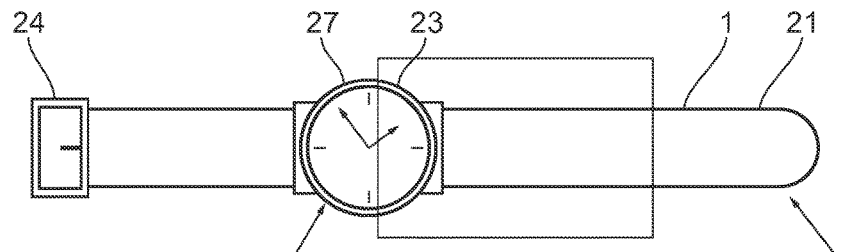
FIG. 2A
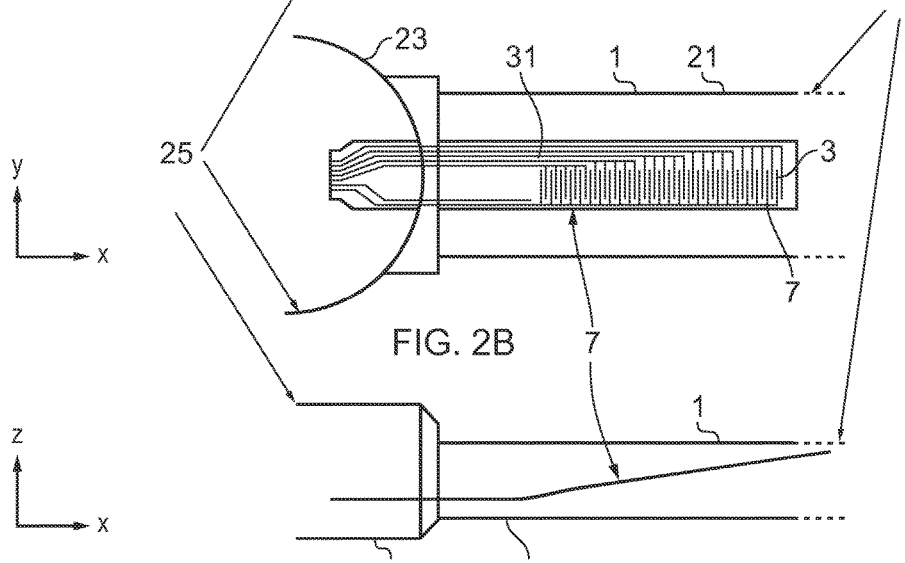
FIG. 2B
FIG. 2C

APPARATUS, METHOD AND COMPUTER PROGRAM FOR DETECTING PHYSIOLOGICAL PARAMETERS

RELATED APPLICATION

This application was originally filed as PCT Application No. PCT/FI2014/050516 filed Jun. 25, 2014, which claims priority benefit from GB Application No. 1312720.4, filed Jul. 16, 2013.

TECHNOLOGICAL FIELD

Examples of the disclosure relate to an apparatus, method and computer program for detecting physiological parameters. In particular, they relate to an apparatus, method and computer program for detecting physiological parameters which may provide an indication of the sweat gland activity of a user.

BACKGROUND

Sensors which may be positioned on or close to the body of a user to measure physiological parameters are known. The outputs from such sensors may be used to monitor the physiological condition of the user for example, during a period of activity or exercise or to assess the user for health purposes or to provide an indication of a user's emotional state or for any other suitable purpose.

Such sensors may be configured to monitor the sweat gland activity of the user. This may be achieved by using a sensor to detect water, or other chemicals present in sweat, in proximity to the user's skin.

It is known to measure sweat gland activity using sensors which measure galvanic skin response. Such sensors may be problematic as they require direct contact with the skin. This may be inconvenient and/or uncomfortable for a user. Also, movement of the sensors relative to the user's skin may lead to motion artefacts in the obtained measurements.

It may be beneficial to provide improved sensors for detecting such physiological parameters.

BRIEF SUMMARY

According to some, but not necessarily all, examples of the disclosure there may be provided an apparatus comprising: a plurality of sensors configured to detect a physiological parameter: wherein at least one first sensor is configured to have a first sensitivity to the physiological parameter and at least one second sensor is configured to have a second sensitivity to the physiological parameter; such that a parameter profile, comprising a plurality of measurements of the physiological parameter at different sensitivities, is provided by the apparatus.

In some examples the parameter profile provided by the apparatus may be configured to be compared to known parameter profiles of the parameter to enable the presence of the parameter to be quantified.

In some examples the apparatus may be configured so that the at least one first sensor and the at least one second sensor are positioned at different distances from a user's skin.

In some examples the apparatus may comprise at least one proximity sensor configured to detect the distance between the user's skin and at least one of the plurality of sensors.

In some examples the apparatus may comprise a temperature sensor.

In some examples at least one third sensor may be configured to have a third sensitivity to the parameter.

In some examples the at least one first sensor may comprise a first sensing material and the at least one second sensor may comprise a second different sensing material.

In some examples at least one of the plurality of sensors may comprise a two dimensional material.

In some examples at least one of the plurality of sensors may comprise at least one of graphene oxide, graphene, functionalised graphene, boron nitride, molybdenite.

In some examples the physiological parameter may give an indication of sweat gland activity of the user.

In some examples the apparatus may be configured to be worn by a user.

According to some, but not necessarily all, examples of the disclosure there may be provided a method comprising: detecting a physiological parameter by a plurality of sensors, wherein at least one first sensor is configured to have a first sensitivity to the physiological parameter and at least one second sensor is configured to have a second sensitivity to the physiological parameter; obtaining a parameter profile comprising a plurality of measurements of the physiological parameter at different sensitivities detected by the plurality of sensors.

In some examples the method may further comprise comparing the obtained parameter profile with a known parameter profiles of the parameter to enable the presence of the parameter to be quantified.

In some examples the at least one first sensor and the at least one second sensor may be positioned at different distances from a user's skin.

In some examples the method may further comprise detecting the distance between the user's skin and at least one of the plurality of sensors using a proximity sensor.

In some examples the method may further comprise determining the temperature of the plurality of sensors using a temperature sensor.

In some examples the at least one third sensor may be configured to have a third sensitivity to the parameter.

In some examples the at least one first sensor may comprise a first sensing material and the at least one second sensor may comprise a second different sensing material.

In some examples at least one of the plurality of sensors may comprise a two dimensional material.

In some examples at least one of the plurality of sensors may comprise at least one of graphene oxide, graphene, functionalised graphene, boron nitride molybdenite.

In some examples the physiological parameter may give an indication of sweat gland activity of the user.

In some examples the plurality of sensors may be provided in an apparatus configured to be worn by a user.

According to some, but not necessarily all, examples of the disclosure there may be provided a computer program comprising computer program instructions that, when executed by processing circuitry, cause at least the following to be performed: detecting a physiological parameter by a plurality of sensors, wherein at least one first sensor is configured to have a first sensitivity to the physiological parameter and at least one second sensor is configured to have a second sensitivity to the physiological parameter; obtaining a parameter profile comprising a plurality of measurements of the physiological parameter at different sensitivities detected by the plurality of sensors.

In some examples there may be provided a computer program comprising computer program instructions for causing a computer to perform the methods described above.

In some examples there may be provided a non-transitory computer readable medium comprising the computer programs as described above.

In some examples there may be provided an electromagnetic carrier signal carrying the computer programs as described above.

The apparatus may be for detecting physiological parameters. In some examples the apparatus may be for detecting physiological parameters which may give an indication of sweat gland activity of the user.

BRIEF DESCRIPTION

Figure 4:
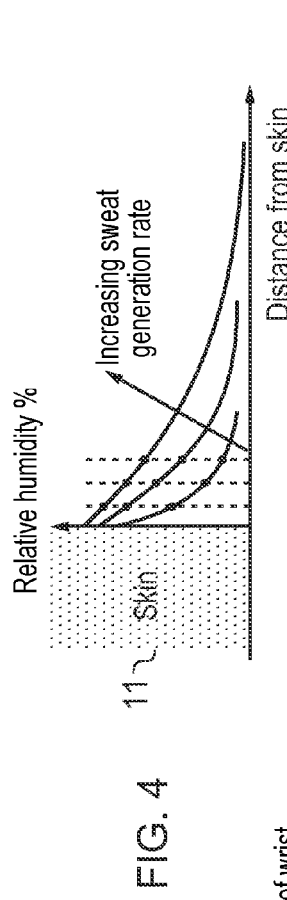
Figure 6:
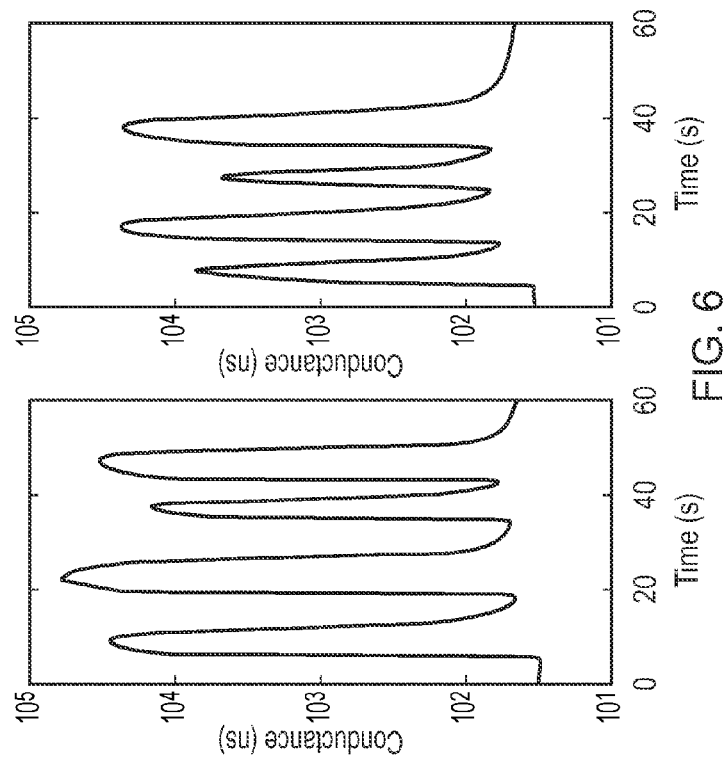
Figure 5:
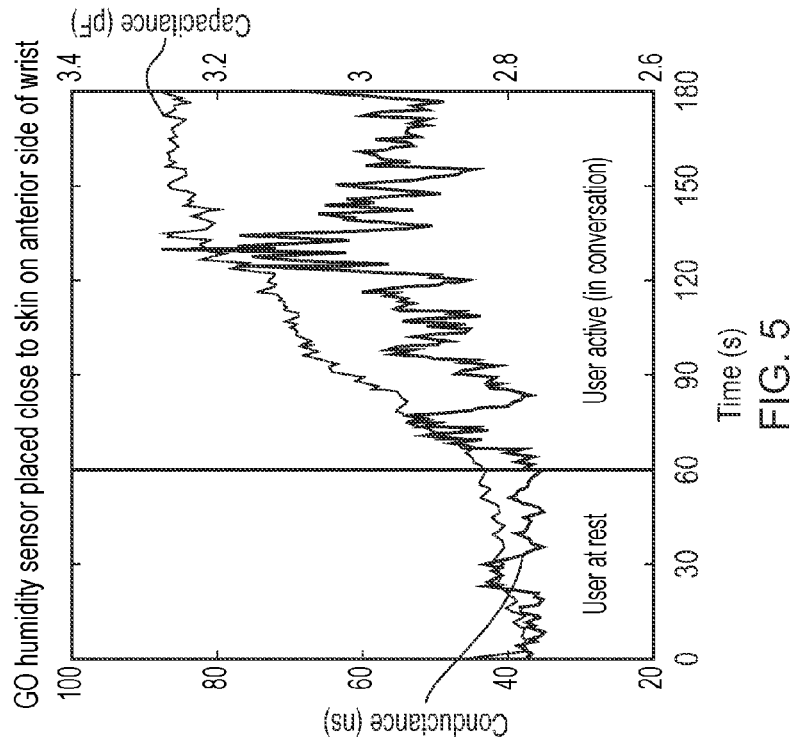
Figure 7:
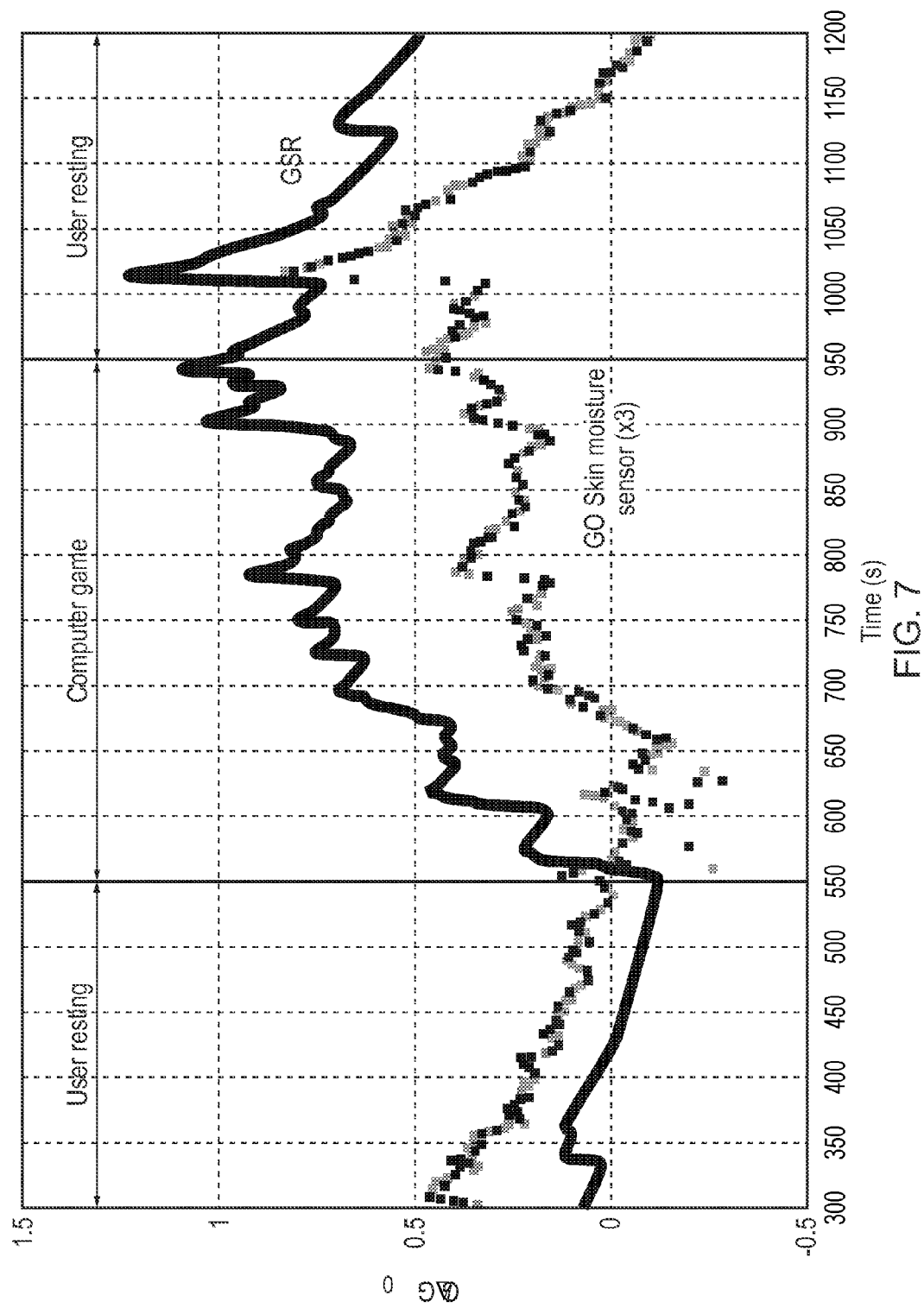
Figure 8:
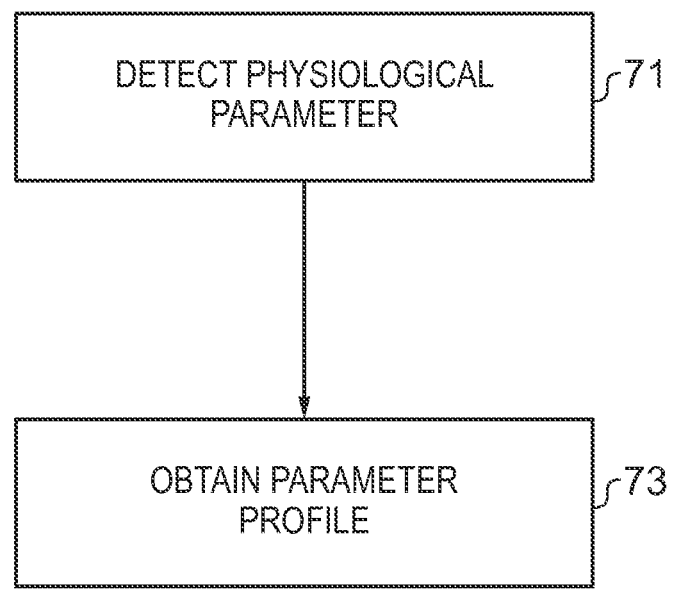

For a better understanding of various examples that are useful for understanding the detailed description, reference will now be made by way of example only to the accompanying drawings in which:

FIG. 1 illustrates an apparatus;
FIGS. 2A to 2C illustrate an apparatus;
FIG. 3 schematically illustrates an apparatus;
FIG. 4 illustrates a plot of results obtained by sensors;
FIG. 5 illustrates a plot of results obtained by sensors;
FIG. 6 illustrates a plot of results obtained by sensors;
FIG. 7 illustrates a plot of results obtained by sensors; and
FIG. 8 illustrates a method.

DETAILED DESCRIPTION

The Figures illustrate an apparatus 1 comprising: a plurality of sensors 3, 5 configured to detect a physiological parameter: wherein at least one first sensor 3, 5 is configured to have a first sensitivity to the physiological parameter and at least one second sensor 3, 5 is configured to have a second sensitivity to the physiological parameter; such that a parameter profile, comprising a plurality of measurements of the physiological parameter at different sensitivities, is provided by the apparatus 1.

FIG. 1 illustrates an example apparatus 1. The apparatus 1 comprises a plurality of sensors 3, 5. The apparatus 1 also comprises a plurality of permeable layers 7.

The apparatus 1 is configured to be positioned adjacent to or in proximity to a user's skin 11. This may enable the sensors 3, 5 to detect physiological parameters. The physiological parameter may be any parameter which relates to the physiology of the user of the apparatus 1. The physiological parameter may be a parameter which is generated by the user of the apparatus 1. In some examples the sensors 3, 5 may be configured to detect water or other chemicals which may be present in sweat. This may enable the apparatus 1 to monitor the activity of a user's sweat glands. The sweat gland activity may be maintained by measuring the concentration of water proximal to the skin occurring through evaporation.

The sweat gland activity of the user may be measured for a range of purposes, in some examples the sweat gland activity may give an indication of the emotional state of a user. This information may then be used to control an electronic device such as a communications device. In other examples the sweat gland activity may give an indication of a user's activity levels, for example during exercise or their general health.

In the example of FIG. 1 the apparatus 1 is positioned adjacent to the skin 11 of the user. The apparatus 1 may be positioned on any suitable part of the user's body, such as their arm, hand or torso.

In some examples the apparatus 1 may comprise attachment means which may enable the apparatus 1 to be secured to the user's body. In some examples the attachment means may comprise a strap which may be attached around a user's arm or leg. In other examples the attachment means may comprise, for example, an adhesive portion which may enable the apparatus 1 to be adhered to the user's skin. In some examples the apparatus 1 may be part of an item of clothing or a head set which may be configured to be worn by the user.

The apparatus 1 in FIG. 1 comprises a plurality of sensors 3, 5. Each of the sensors 3, 5 may be configured to detect a physiological parameter. Each of the sensors 3, 5 may be configured to detect the same physiological parameter.

In the example of FIG. 1 the apparatus 1 comprises four sensors 3, 5. It is to be appreciated that different numbers of sensors 3, 5 could be provided in other examples of the disclosure.

The sensors 3, 5 may comprise any material which may be configured to be sensitive to a physiological parameter. In examples where the apparatus 1 is configured to measure the skin hydration of a user the physiological parameter could be water, the concentration of water, or any other chemical which may be detected in the sweat of the user.

The sensors 3, 5 may have any suitable transduction mechanism for detecting a parameter and providing an electrical input signal. In some examples the sensors 3, 5 may have a capacitive or a conductive transduction mechanism. If the sensor 3, 5 has a capacitive transduction mechanism then the presence of the physiological parameter may change the permittivity of the material in the sensor, 3, 5. The capacitance of the sensor 3, 5 may have a known variation as a function of the concentration of the physiological parameter In such examples the sensor 3, 5 may comprise a material such as polymeric material or any other suitable material.

If the sensor 3, 5 has a conductive transduction mechanism then the presence of the sensed physiological parameter may change the conductivity of the material. The conductance of the sensor 3, 5 may have a known variation as a function of the concentration of the physiological parameter. In such examples the sensor 3, 5 may comprise a material such as graphene oxide, graphene, functionalised graphene materials, boron nitride, molybdenite or any other suitable material. In some examples the sensor material may comprise a two dimensional material.

It is to be appreciated that other transduction mechanisms could be used in other examples. For example, the sensor 3, 5 may comprise a concentration cell that produces a built-in potential as a function of humidity. In other examples a graphene field effect transistor may be used to transduce changes in the local dielectric environment due to the presence of the physiological parameter.

The material which is chosen for the sensor 3, 5 may depend on the physiological parameter which is to be detected. In some examples the same material may be used for each of the plurality of sensors 3, 5. In some embodiments different materials may be used for each of the sensors 3, 5.

In the example of FIG. 1 a first sensor 5 is provided. The first sensor 5 may be configured to detect a physiological parameter but also to act as a proximity sensor. The proximity sensor 5 may provide an indication of the distance between the first sensor 5 and the user's skin 11.

In the example of FIG. 1 only one proximity sensor 5 is provided. This sensor 5 gives an indication of the distance between the first sensor 5 and the user's skin 11. The distance between the other sensors 3 and the user's skin 11 may be obtained from this indication. In other examples a plurality of proximity sensors may be provided so that the distance between a plurality of different sensors and the user's skin 11 may be measured.

In the particular example of FIG. 1 the proximity sensor is integrated into the first sensor 5. This sensor may be configured to detect both the physiological parameter and the distance between the sensor 5 and the user's skin 11. In such examples the sensor material may have a conductive transduction mechanism for sensing the physiological parameter and may have a capacitance which does not vary in response to the physiological parameter. For example, a layer of graphene oxide with a thickness of less than 20 nm may have a negligible capacitive response to humidity but may have a very sensitive conductance response. In such examples, the sensor 5 may be configured to act as a capacitive proximity sensor and a conductive parameter sensor.

In other examples separate proximity sensors may be provided within the apparatus 1. The separate proximity sensors might not be configured to detect the physiological parameters.

In FIG. 1 sensors 3, 5 are arranged in a stack. The sensors 3, 5 are arranged so that they overlay each other. When the apparatus 1 is attached to the user's skin 11 each of the sensors covers the same portion of the user's skin 11 and so detects the same physiological parameter from the same location on the user's body. However each sensor has a different separation from the user's skin 11 and so provides a different response to detected physiological parameters.

In the example of FIG. 1 the sensors 3, 5 have different distances from the user's skin 11. The response of the sensors 3, 5 to the physiological parameter may depend on the distance between the sensor 3, 5 and the user's skin 11, as indicated by the plot 15. As the sensors 3, 5 are each positioned at different distances from the user's skin 11, each of the sensors 3, 5 have different sensitivities in that they provide different outputs for the same level of physiological parameter. In particular at least one sensor 3, 5 may have a first sensitivity to the physiological parameter and at least one second sensor 3, 5 may have a second sensitivity to the physiological parameter. In some examples there may also be provided a third sensor which may have a third sensitivity to the physiological parameter. This may enable the apparatus 1 to provide a plurality of different measurements of the same physiological parameter.

The apparatus 1 of FIG. 1 also comprises a plurality of permeable layers 7. The layers 7 may be permeable or semi-permeable. The permeable layers 7 may comprise any material which substances to pass through to enable the physiological parameter to be detected. In examples where the apparatus 1 is configured to measure the skin hydration of the user the permeable layers 7 may enable moisture exchange with the user's skin 11.

The permeable layers 7 may be made of any suitable material such as a porous film. The permeable layers 7 may be flexible to enable the apparatus 1 to be bent or otherwise deformed. This may make the apparatus 1 easier to attach to a user's body and/or more comfortable for the user to wear.

A first permeable layer 7 may be provided between the first sensor 5 and the users skin 11. This may prevent the first sensor 5 from coming into direct contact with the user's skin 11. This may keep the first sensor 5 at a first distance from the user's skin 11.

A plurality of other permeable layers 7 may be provided so that there is at least one permeable layer 7 between each of the plurality of sensors 3, 5. In some examples the sensors 3, 5 may also be permeable. For example, where the apparatus 1 is configured to detect water a water permeable graphene oxide film may be used as the sensing material. The graphene oxide film may be deposited on a permeable substrate. The permeable substrate could be, for example, a microporous breathable polymer film or any other suitable material.

In some examples the apparatus 1 may also comprise an impermeable layer 9. The impermeable layer may be provided between the plurality of sensors 3, 5 and the external environment. The impermeable layer 9 may be impermeable to the physiological parameter which is detected by the sensors 3, 5. This may prevent, for example, water or other chemicals in the environment 13 being detected by the sensor as this would affect the measurements obtained by the apparatus 1.

In some examples the apparatus 1 may comprise a temperature sensor. The temperature sensor may be configured to determine the temperature of the sensors 3, 5 and allow the measurements of the sensors to be adjusted accordingly.

In some examples the apparatus may comprise a sensor which may be configured to detect ambient humidity and temperature. This may enable emotional responses of the physiological parameter to be distinguished from climatic response.

FIGS. 2A to 2C illustrate another example apparatus 1. In this example apparatus 1 a plurality of sensors 3 may be integrated into the strap 21 of a watch 23. FIG. 2A illustrates an example watch 23, FIG. 2B detailed view of the underside of the watch 23 and FIG. 2C illustrates a cross section through the watch 23.

The watch 23 comprises a rigid portion 25 and a strap 21. The rigid portion 25 may comprise the watch face 27. In some examples the rigid portion 25 may also house processing circuitry. The processing circuitry may be configured to collect and/or analyse the measurements of the plurality of sensors 3. In some examples the rigid portion may comprise communication means such as a receiver and/or transceiver. The communication means may enable measurements obtained by the sensors 3 to be provided to an additional device. The additional device may then be able to analyse the measurements obtained by the sensors 3.

The strap 21 may provide attachment means which enables the apparatus 1 to be worn by the user. The strap 21 may enable the watch to be secured to the user's body. The strap 21 also comprises a fastener 29 which enables the watch to be held securely in position around the user's wrist. The strap 21 may enable the watch 23 to be positioned adjacent to the user's skin 11.

In FIG. 2B the plurality of sensors 3 may be provided on the underside of the strap 21. The plurality of sensors 3 may be provided on the strap 21 so that when the user is wearing the watch 23 the sensors 3 are in proximity with the user's skin 11. It is to be appreciated that in other examples the sensors 3 could be positioned on other portions of the watch 23 such as the rigid portion 25.

In FIG. 2B the sensors 3 extend in a horizontal direction as indicated by the x axis. The z axis extends out of the page. In the particular example of FIG. 2B the sensors 3 extend along the length of the watch strap 21. In other examples the sensors 3 could be arranged to extend along the width of the watch strap 21 in the y direction.

As illustrated in FIG. 2B a plurality of connection means 31 are also provided. The connection means 31 may be configured to connect the sensors 3 to processing circuitry which may be housed in the rigid portion 25. The connection means may comprise, for example, a plurality of conductive traces.

A permeable layer 7 is provided overlaying the sensors 3. The sensors 3 and the permeable layer 7 may be as described above in relation to FIG. 1. The permeable layer 7 may act as a spacer between the sensors 3 and the user's skin 11. The permeable layer 7 may be configured to maintain a separation between the user's skin 11 and the plurality of sensors 3.

The thickness of the permeable layer 7 may be different for different portions of the array of sensors 3. FIG. 2C is a cross section of the example watch strap 21 which illustrates the variation in thickness of the permeable layer 7.

In the example of FIG. 2C the thickness of the permeable layer 7 increases linearly with distance in the x direction. The thickness of the permeable layer 7 determines the distance between each of the sensors 3 and the user's skin 11. Where the permeable layer 7 is thicker the sensors 3 have a larger separation from the user's skin 11 than where the permeable layer 7 is thinner. This enables the distance between the sensors 3 and the user's skin to be controlled by selecting the thickness of the permeable layer 7. The thickness of the permeable layer 7 may be selected so that different sensors have a different separation from the user's skin 11.

The response of the sensors 3 to the physiological parameter may depend on the distance between the sensor 3 and the user's skin 11. If the permeable layer 7 is configured so that the sensors 3 are each positioned at different distances from the user's skin 11, then the sensors 3 have different sensitivities in that they provide different outputs for the same level of physiological parameter.

In the example of FIGS. 2A to 2C the sensors 3 may be positioned close to each other in the x and y directions. As the sensors 3 are positioned adjacent to each other rather than overlaying each other, as in FIG. 1, the sensors 3 are not detecting the physiological parameter from the same piece of skin. There may be natural variations of the physiological parameters of a user across the areas of their skin, for example there may be a higher concentration of sweat glands on the underside of the wrist than on the upper side of the wrist. Positioning the sensors 3 close to each other will reduce the effects of this variation.

FIG. 3 schematically illustrates an apparatus 1 according to examples of the disclosure. The apparatus 1 may be an apparatus 1 as described above in relation to FIGS. 1 and 2A to 2C.

The apparatus 1 may comprise a plurality of sensors 3. The sensor 3 may be as configured to detect a physiological parameter as described above in relation to FIGS. 1 and 2. The sensors 3 may be arranged in any suitable arrangement. The sensors 3 may also comprise proximity sensors 5 and/or temperature sensors.

The apparatus 1 may comprise controlling circuitry 43. The controlling circuitry 43 may comprise one or more controllers. The controlling circuitry 43 may be implemented using instructions that enable hardware functionality, for example, by using executable computer program instructions in a general-purpose or special-purpose processing circuitry 47 that may be stored on a computer readable storage medium (disk, memory etc) to be executed by such processing circuitry 47.

The controlling circuitry 43 may comprise processing circuitry 47 and memory circuitry 49. The processing circuitry 47 may be configured to read from and write to the memory circuitry 49. The processing circuitry 47 may comprise one or more processors. The processing circuitry 47 may also comprise an output interface via which data and/or commands are output by the processing circuitry 47 and an input interface via which data and/or commands are input to the processing circuitry 47.

The memory circuitry 49 may be configured to store a computer program 53 comprising computer program instructions 51 (computer program code) that controls the operation of the apparatus 1 when loaded into processing circuitry 47. The computer program instructions, of the computer program 53, provide the logic and routines that enables the apparatus 1 to perform the methods illustrated in FIG. 7. The processing circuitry 47 by reading the memory circuitry 49 is able to load and execute the computer program 53.

The computer program may arrive at the apparatus via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), an article of manufacture that tangibly embodies the computer program. The delivery mechanism may be a signal configured to reliably transfer the computer program. The apparatus may propagate or transmit the computer program as a computer data signal.

Although the memory circuitry is illustrated as a single component it may be implemented as one or more separate components some or all of which may be integrated/removable and/or may provide permanent/semi-permanent/dynamic/cached storage.

Although the processing circuitry is illustrated as a single component it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:

(a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device."

The controlling circuitry may be positioned remotely from the sensors 3. For example, in the apparatus 1 of FIGS. 2A to 2C the sensors 3 are positioned on the strap 21 while the controlling circuitry 43 may be positioned within the rigid housing 25. Connection means may be configured to connect the controlling circuitry 43 to the sensors 3.

In the example FIG. 3 an output device 41 is provided. The controlling circuitry may be configured to analyse the measurements obtained by the sensors 3 and provide a control signal to the output device 21. In some examples the output device 41 could be a personal electronics device such as a mobile telephone. This may enable apparatus 1 to detect a physiological parameter and control the output device 41 accordingly. The physiological parameter may provide an indication of the emotional state of the user and so the apparatus 1 may enable the user's emotional state to be detected and used to control an output device 41.

FIG. 4 illustrates example parameter profiles which may be obtained using example apparatus 1 as described above in relation to FIGS. 1 to 3. In this example the parameter is the humidity.

Each parameter profile may comprise a plurality of measurements of the physiological parameter at different sensitivities. The parameter profile may comprise a plurality of different measurements which may be obtained by different sensors 3. The sensors 3 provide a different response for the same production of physiological parameter from the skin.

In the example of FIG. 4 three measurement points are provided. These may be provided by three different sensors 3. The parameter profile may then be extrapolated from the measurement points. It is to be appreciated that in other examples more than three sensors may be used and this may lead to a more accurate measurement of the physiological parameter.

In the example of FIG. 4 the different sensors 3 are provided at different distances from the user's skin 11. The distances of the sensors 3 from the user's skin 11 may be determined using one or more proximity sensors. The responsiveness of the sensors 3 as a function of distance from the skin 11 may be known and so by comparing the obtained parameter profile to known parameter profiles the concentration of the parameter can be measured.

In other examples the plurality of sensors 3 may comprise different materials. The different materials may have different sensitivities to the physiological parameter and so may provide a plurality of different responses. The plurality of responses obtained from the sensors 3 may then be extrapolated into a profile. The parameter profile which is obtained from the plurality of sensors 3 may be compared to known profiles in order to quantify the presence of the physiological parameter.

Measuring the concentration of the physiological parameter may enable a physiological characteristic, such as the sweat gland activity, the skin hydration of the user or any other suitable characteristic, to be determined.

The variation of either the conductance or the capacitance of the sensors 3 may be measured to monitor the presence of the physiological parameter. The variable which is measured may depend on the material of the sensors 3 and the parameter which is to be monitored.

FIG. 5 illustrates example plots of capacitance and conductance obtained from a graphene oxide sensor. To obtain the results indicated in FIG. 5 the sensor 3 was mounted on a watch strap 21 and was separated from a user's skin 11 by about 3 mm. The user was resting from 0 s to 60 s and from 60 s to 180 s was engaged in highly stimulating conversation. It can be seen that engaging in conversation produces a change in the user's sweat gland activity which can be detected by the sensors 3.

This may enable the apparatus 1 described above to be used to distinguish between a user at rest and an intellectually stimulated user. The apparatus may also be used to detect when the user is undergoing other forms of stress such as physical activity, cognitive activity, fear response, shock response, or any other suitable stimulation.

FIG. 6 is a plot of the conductance response of a graphene oxide sensor when a finger was placed close to the sensor. In each case a finger was placed close to the sensor four times alternating between dry and wet fingers (dry-wet-dry-wet). In the left hand side plot the separation between the sensor and the finger was approximately 2 mm. In the right hand side plot the separation between the sensor and the finger was approximately 5 mm. It can be seen that the responsiveness of the graphene oxide sensors varies as a function of distance from the skin. This may enable a plurality of different sensors 3 arranged at a plurality of different distances from the skin to be used to obtain measurements to create a parameter profile.

FIG. 7 is a plot which compares the response between a Galvanic skin response sensor (GSR) and a Graphene Oxide (GO) sensor. From 300 to 550 seconds the user was resting, from 550 to 950 seconds the user was playing a simple computer game (similar to Space Invaders) and from 950 to 1200 seconds the user was resting. In these examples the graphene oxide sensor was positioned approximately 1 mm from the palm of the user. It can be seen from this plot that there is a correlation between the response of graphene oxide sensor and the GSR sensor which indicates that the graphene oxide sensor can be used to monitor sweat gland activity.

FIG. 8 illustrates a method according to examples of the disclosure. The method may be implemented by apparatus such as those illustrated in FIGS. 1 to 3.

The method may comprise detecting, at block 71 a physiological parameter by a plurality of sensors 3. The sensors 3 may be arranged as described above so that at least one first sensor 3 is configured to have a first sensitivity to the physiological parameter and at least one second sensor 3 is configured to have a second sensitivity to the physiological parameter.

The method also comprises obtaining, at block 73 a parameter profile comprising a plurality of measurements of the physiological parameter at different sensitivities detected by the plurality of sensors. The parameter profile may then be compared with other known profiles to enable the presence of the parameter to be quantified.

The example apparatus 1 described above provides an apparatus 1 which may be used to measure the sweat gland activity, or other physiological characteristics, of a user. The sensors 3 of the apparatus 1 do not need to be positioned in direct contact with a user's skin 11 in contrast to methods which require galvanic conductance measurements. This may be advantageous as it may be uncomfortable for a user to have electrodes positioned on their skin 11. Also it may difficult to keep the electrodes in exactly the same location which may lead to artefacts in measurements made by such sensors.

Also as a plurality of sensors 3 with different sensitivities are arranged to measure the same parameter the apparatus 1 may have a large dynamic range. The saturation of the apparatus 1 may be avoided when there is a high concentration of the physiological parameter but the apparatus 1 may also be able to detect a low concentration of the physiological parameter.

The blocks illustrated in the FIG. 8 may represent steps in a method and/or sections of code in the computer program 53. The illustration of a particular order to the blocks does not necessarily imply that there is a required or preferred order for the blocks and the order and arrangement of the block may be varied. Furthermore, it may be possible for some blocks to be omitted.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class.

In the above description the term coupled means operationally coupled and any number or combination of intervening elements can exist including no intervening elements.

Although embodiments of the present invention have been described in the preceding paragraphs with reference to various examples, it should be appreciated that modifications to the examples given can be made without departing from the scope of the invention as claimed. For example, in the above description the sensitivities of the sensors may be arranged to be different by having different sensors at different separations from the skin of the user. In other examples the different sensitivities may be achieved by having different materials in the sensors.

In other examples the same material may be used but the level of oxidation may be changed to change the sensitivities.

In the above described examples the sensors 3 are provided on a watch strap. In other examples the sensors 3 could be provided, for example, in clothing or frames of glasses or headsets.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
   a plurality of sensors configured to detect a physiological parameter;
   wherein at least one first sensor is configured to have a first sensitivity to the physiological parameter and at least one second sensor is configured to have a second sensitivity to the physiological parameter;
   a permeable layer located between the at least one first sensor and a user's skin, the permeable layer being configured to enable moisture exchange between the at least one first sensor and the user's skin;
   a parameter profile sensor, wherein the parameter profile sensor, with the at least one first sensor and the at least one second sensor, provides a parameter profile comprising a plurality of measurements of the physiological parameter at different sensitivities;
   wherein the at least one first sensor and the at least one second sensor each provide a different response for a production of the physiological parameter; and
   wherein the at least one first sensor and the at least one second sensor are arranged in a stack and overlay each other.

2. An apparatus as claimed in claim 1 wherein the parameter profile provided using the apparatus is configured to be compared to one or more known parameter profiles of the parameter to enable the physiological parameter to be quantified.

3. An apparatus as claimed in claim 1 wherein the apparatus is configured so that the at least one first sensor and the at least one second sensor are positioned at different distances from the user's skin.

4. An apparatus as claimed in claim wherein the apparatus comprises at least one proximity sensor configured to detect the distance between the user's skin and at least one of the plurality of sensors.

5. An apparatus as claimed in claim 1 wherein the apparatus comprises a temperature sensor.

6. An apparatus as claimed in claim 1, wherein at least one third sensor is configured to have a third sensitivity to the physiological parameter.

7. An apparatus as claimed in claim wherein the at least one first sensor comprises a first sensing material and the at least one second sensor comprises a second different sensing material.

8. An apparatus as claimed in claim 1 wherein at least one of the plurality of sensors comprises a two dimensional material.

9. An apparatus as claimed in claim 1 wherein at least one of the plurality of sensors comprises at least one of graphene oxide, graphene, functionalised graphene, boron nitride, and molybdenite.

10. An apparatus as claimed in claim 1 wherein the physiological parameter gives an indication of sweat gland activity of the user.

11. An apparatus as claimed in claim 1 wherein the apparatus is configured to be worn by a user.

12. A method comprising:
    detecting a physiological parameter using a plurality of sensors, wherein at least one first sensor is configured to have a first sensitivity to the physiological parameter and at least one second sensor is configured to have a second sensitivity to the physiological parameter, wherein a permeable layer is located between the at least one first sensor and a user's skin, the permeable layer being configured to enable moisture exchange between the at least one first sensor and the user's skin; and obtaining a parameter profile using a parameter profile provider, wherein the parameter profile comprises a plurality of measurements of the physiological parameter at different sensitivities detected using the plurality of sensors;

wherein the at least one first sensor and the at least one second sensor each provide a different response for a production of the physiological parameter; and wherein the at least one first sensor and the at least one second sensor are arranged in a stack and overlay each other.

13. A method as claimed in claim 12 further comprising comparing the obtained parameter profile with one or more known parameter profiles of the parameter to enable the physiological parameter to be quantified.

14. A method as claimed in claim 12 wherein the at least one first sensor and the at least one second sensor are positioned at different distances from the user's skin.

15. A method as claimed in claim 14 further comprising detecting the distance between the user's skin and at least one of the plurality of sensors using a proximity sensor.

16. A method as claimed in claim 12 further comprising determining a temperature of the plurality of sensors using a temperature sensor.

17. A method as claimed in claim 12 wherein at least one third sensor is configured to have a third sensitivity to the physiological parameter.

18. A method as claimed in claim 12 wherein the at, least one first sensor comprises a first sensing material and the at least one second sensor comprises a second different sensing material.

19. A method as claimed in claim 12 wherein at least one of the plurality of sensors comprise a two dimensional material.

20. A method as claimed in claim 12 wherein at least one of the plurality of sensors comprises at least one of graphene oxide, graphene, functionalised graphene, boron nitride, and molybdenite.

21. A method as claimed in claim 12 wherein the physiological parameter gives an indication of sweat gland activity of the user.

22. A method as claimed in claim 12 wherein the plurality of sensors are provided in an apparatus configured to be worn by a user.

23. An apparatus, comprising:
at least one processor; and
at least one non-transitory memory including computer program code, the at least one memory and the computer program code configured to, with the at least one processor, cause the apparatus at least to perform:
detecting a physiological parameter using a plurality of sensors, wherein at least one first sensor is configured to have a first sensitivity to the physiological parameter and at least one second sensor is configured to have a second sensitivity to the physiological parameter, wherein a permeable layer is located between the at least one first sensor and a user's skin, the permeable layer being configured to enable moisture exchange between the at least one first sensor and the user's skin; and obtaining a parameter profile using a parameter profile sensor, wherein the parameter profile sensor, with the at least one first sensor and the at least one second sensor, provides a parameter profile comprising a plurality of measurements of the physiological parameter at different sensitivities detected using the plurality of sensors;

wherein the at least one first sensor and the at least one second sensor each provide a different response for a production of the physiological parameter; and wherein the at least one first sensor and the at least one second sensor are arranged in a stack and overlay each other.

* * * * *